US00PP19165P2

(12) United States Plant Patent
Takahata et al.

(10) Patent No.: US PP19,165 P2
(45) Date of Patent: Sep. 2, 2008

(54) ***IPOMOEA* PLANT NAMED 'KYUIKUKAN 4'**

(50) Latin Name: *Ipomoea batatas*
Varietal Denomination: Kyuikukan 4

(75) Inventors: Yasuhiro Takahata, Miyakonojo (JP); Masaru Yoshinaga, Miyakonojo (JP); Hiroki Nakayama, Miyakonojo (JP); Masaru Tanaka, Miyakonojo (JP); Yoshinori Nakazawa, Kumamoto (JP); Toru Kumagai, Tsukuba (JP); Yumi Kai, Miyakonojo (JP); Kenji Katayama, Miyakonojo (JP); Tetsufumi Sakai, Miyakonojo (JP); Yasuyuki Murakami, Shiga (JP); Kazunari Iwaki, Kanagawa (JP)

(73) Assignee: Suntory Flowers Ltd, Tokyo (JP)

( * ) Notice: Subject to any disclaimer, the term of this patent is extended or adjusted under 35 U.S.C. 154(b) by 0 days.

(21) Appl. No.: 11/800,782

(22) Filed: May 7, 2007

(51) Int. Cl.
*A01H 5/00* (2006.01)

(52) U.S. Cl. ..... Plt./258

(58) Field of Classification Search ..... Plt./258
See application file for complete search history.

*Primary Examiner*—Kent L. Bell
*Assistant Examiner*—Annette H Para
(74) *Attorney, Agent, or Firm*—C. A. Whealy

(57) ABSTRACT

A new and distinct cultivar of *Ipomoea* plant named 'Kyuikukan 4', characterized by its compact and outwardly trailing growth habit and dark green-colored foliage.

1 Drawing Sheet

Botanical designation: *Ipomoea batatas.*
Cultivar denomination: 'Kyuikukan 4'.

BACKGROUND OF THE INVENTION

The present invention relates to a new and distinct cultivar of *Ipomoea,* botanically known as *Ipomoea batatas,* and hereinafter referred to by the name 'Kyuikukan 4'.

The new *Ipomoea* is a product of a planned breeding program conducted by the Inventors in Miyazaki, Japan. The objective of the breeding program is to create new compact *Ipomoea* cultivars with attractive foliage shape and coloration.

The new cultivar originated from an open-pollination made by the Inventors in September, 2000 of a proprietary selection of *Ipomoea batatas* identified as code number KOP98211-2, not patented, as the female, or seed, parent with an unknown selection of *Ipomoea batatas* as the male, or pollen, parent. The cultivar Kyuikukan 4 was discovered and selected by the Inventors as a single plant within the progeny of the stated open-pollination in a controlled environment in Miyazaki, Japan.

Asexual reproduction of the new *Ipomoea* by terminal cuttings in a controlled environment in Miyazaki, Japan since December, 2005, has shown that the unique features of this new *Ipomoea* are stable and reproduced true to type in successive generations.

SUMMARY OF THE INVENTION

The cultivar Kyuikukan 4 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kyuikukan 4'. These characteristics in combination distinguish 'Kyuikukan 4' as a new and distinct cultivar of *Ipomoea:*

1. Compact and outwardly trailing growth habit.
2. Dark green-colored foliage.

Plants of the new *Ipomoea* can be compared to plants of the female parent selection. Plants of the new *Ipomoea* differ from plants of the female parent selection primarily in flower production as plants of the new *Ipomoea* are day-neutral whereas plants of the female parent selection only flower under short day photoinductive conditions.

Plants of the new *Ipomoea* can be compared to plants of the *Ipomoea batatas* cultivar Sweet Caroline Bronze, disclosed in U.S. Plant Pat. No. 15,437. In side-by-side comparisons conducted in Shiga, Japan, plants of the new *Ipomoea* differed from plants of the cultivar Sweet Caroline Bronze in the following characteristics:

1. Plants of the new *Ipomoea* were taller and had longer internodes than plants of the cultivar Sweet Caroline Bronze.
2. Plants of the new *Ipomoea* and the cultivar Sweet Caroline Bronze differed in leaf and petiole color.
3. Plants of the new *Ipomoea* had shorter leaf petioles than plants of the cultivar Sweet Caroline Bronze.
4. Plants of the new *Ipomoea* were day-neutral whereas plants of the cultivar Sweet Caroline Bronze flowered only under short day photoinductive conditions.

BRIEF DESCRIPTION OF THE PHOTOGRAPHS

The accompanying colored photographs illustrate the overall appearance of the new *Ipomoea,* showing the colors as true as it is reasonably possible to obtain in colored reproductions of this type. Colors in the photographs may differ slightly from the color values cited in the detailed botanical description which accurately describe the colors of the new *Ipomoea.*

The photograph at the top of the sheet comprises a side perspective view of a typical plant of 'Kyuikukan 4' grown in a container.

The photograph in the middle of the sheet comprises a close-up view of typical leaves of 'Kyuikukan 4'.

The photograph at the bottom of the sheet is a close-up view of a typical open flower of 'Kyuikukan 4'.

DETAILED BOTANICAL DESCRIPTION

The photographs and following observations, measurements and values describe plants grown in Shiga, Japan in a polyethylene-covered greenhouse during the spring under conditions which closely approximate commercial production. During the production of the plants, day temperatures were about 25° C. and night temperatures were about 15° C. Plants were about four months old when the photographs and the description were taken. In the detailed description, color references are made to The Royal Horticultural Society Colour Chart, 2001 Edition, except where general terms of ordinary dictionary significance are used.

Botanical classification: *Ipomoea batatas* cultivar Kyuikukan 4.

Parentage:

*Female, or seed, parent.*—Proprietary selection of *Ipomoea batatas* identified as code number KOP98211-2, not patented.

*Male, or pollen, parent.*—Unknown selection of *Ipomoea batatas,* not patented.

Propagation:

*Type.*—By terminal cuttings.

*Time to initiate roots.*—About three days at temperatures of 20° C. to 25° C.

*Time to produce a rooted young plant.*—About four weeks at temperatures of 20° C. to 25° C.

*Root description.*—Thick, fleshy. Development of tubers, ellipsoidal in shape and light brown in color, has been observed.

Plant description:

*Plant habit.*—Compact and outwardly trailing plant habit. Freely branching habit; pinching enhances lateral branch development; vigorous growth habit.

*Plant height.*—About 15.7 cm.

*Plant diameter.*—About 34.6 cm.

Lateral branch description:

*Length.*—About 20.4 cm.

*Diameter.*—About 3.5 mm.

*Internode length.*—About 2.2 cm.

*Strength.*—Strong.

*Texture.*—Pubescent.

*Color.*—N186C.

Foliage description:

*Arrangement.*—Alternate, simple.

*Length.*—About 11.2 cm.

*Width.*—About 9.5 cm.

*Shape.*—Roughly palmate.

*Apex.*—Acute.

*Base.*—Truncate with cordate tendencies.

*Margin.*—Entire; deeply lobed.

*Texture, upper and lower surfaces.*—Sparsely pubescent.

*Venation pattern.*—Palmate.

*Color.*—Developing foliage, upper surface: 144A; tinted with N77B. Developing foliage, lower surface: 144B. Fully expanded foliage, upper surface: Close to 147A; venation, 144A tinted with N186C. Fully expanded foliage, lower surface: Close to 147B; venation, 144A tinted with N186C.

*Petiole.*—Length: About 6.9 cm. Diameter: About 2.2 mm. Texture, upper and lower surfaces: Sparsely pubescent. Color, upper surface: N186C. Color, lower surface: N77B.

Flower description:

*Flower arrangement and habit.*—Single salverform flowers arising from leaf axils. Freely flowering habit with usually about five to seven flowers and flower buds per lateral branch. Flowers not persistent. Flowers face mostly upright. Flowers not fragrant.

*Natural flowering season.*—Plants of the new *Ipomoea* flower year-round, but in the garden, from summer to fall in Japan.

*Flowering longevity.*—Individual flowers last about one day on the plant.

*Flower diameter.*—About 5.3 cm.

*Flower length* (*depth*).—About 4 cm.

*Throat diameter.*—About 1.9 cm.

*Tube diameter.*—About 1.4 mm.

*Flower bud.*—Shape: Lenticular. Length: About 2.5 cm. Diameter: About 6.7 mm. Color: 76C.

*Corolla.*—Arrangement: Five petals fused at the base and opening into a flared trumpet. Petal length from throat: About 1.6 cm. Petal width: About 2.1 cm. Petal shape: Roughly spatulate. Petal apex: Rounded acute. Petal margin: Entire. Petal texture, upper and lower surfaces: Smooth, glabrous. Color: Petal, when opening, upper and lower surfaces: Close to 76C; throat, N78A. Petal, fully opened, upper and lower surfaces: Close 76C; tube, 76A.

*Calyx.*—Arrangement: One star-shaped calyx tube with five sepals fused at the base per flower. Sepal length: About 1 cm. Sepal width: About 3.5 mm. Sepal shape: Lanceolate. Sepal apex: Acute. Sepal base: Obtuse. Sepal margin: Entire. Color, immature and mature, upper surface: N144A. Color, immature and mature, lower surface: N144A.

*Peduncles.*—Length: About 3.4 cm. Diameter: About 2.6 mm. Angle: Upright. Texture: Smooth. Color: N186C.

*Reproductive organs.*—Stamens: Quantity/arrangement: Five per flower. Anther shape: Ellipsoidal. Anther size: About 2 mm by 4 mm. Anther color: 155D. Pollen amount: Scarce. Pollen color: 155B. Pistils: Quantity: One per flower. Pistil length: About 2 cm. Style color: Towards the base, N80C: towards the apex, 155B. Stigma color: 155B. Seed/fruit: Seed and fruit development have not been observed on plants of the new *Ipomoea.*

Temperature tolerance: Plants of the new *Ipomoea* have been observed to tolerate temperatures from about 5° C. to about 35° C.

Pathogen/pest resistance: Plants of the new *Ipomoea* have not been observed to be resistant to pests and pathogens common to *Ipomoea.*

It is claimed:

1. A new and distinct *Ipomoea* plant named 'Kyuikukan 4' as illustrated and described.

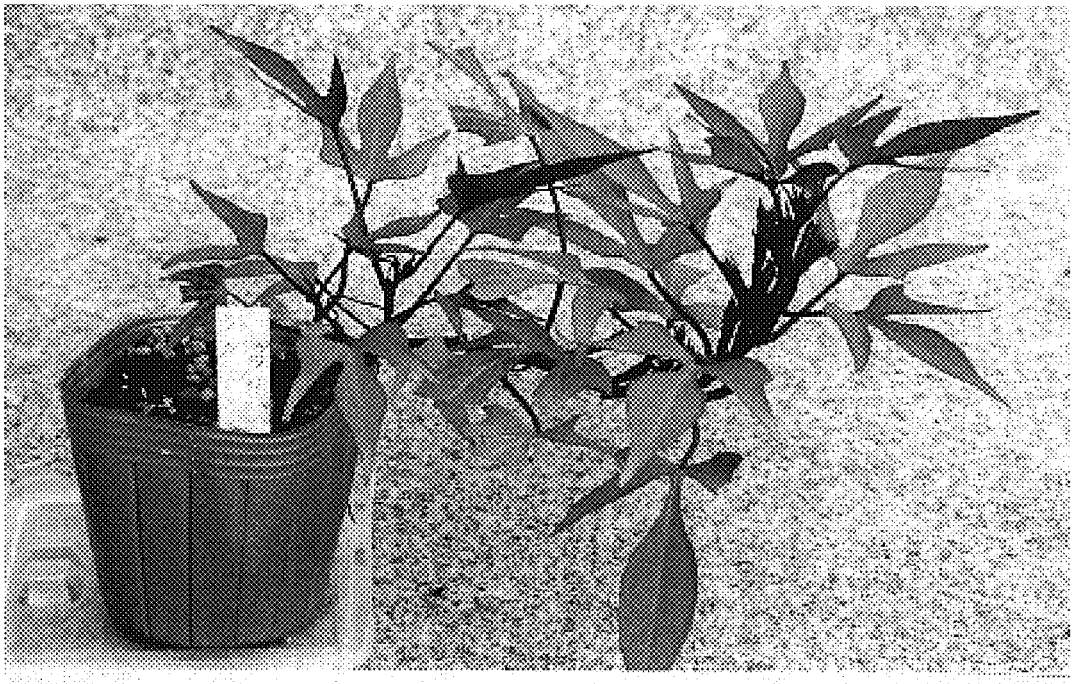
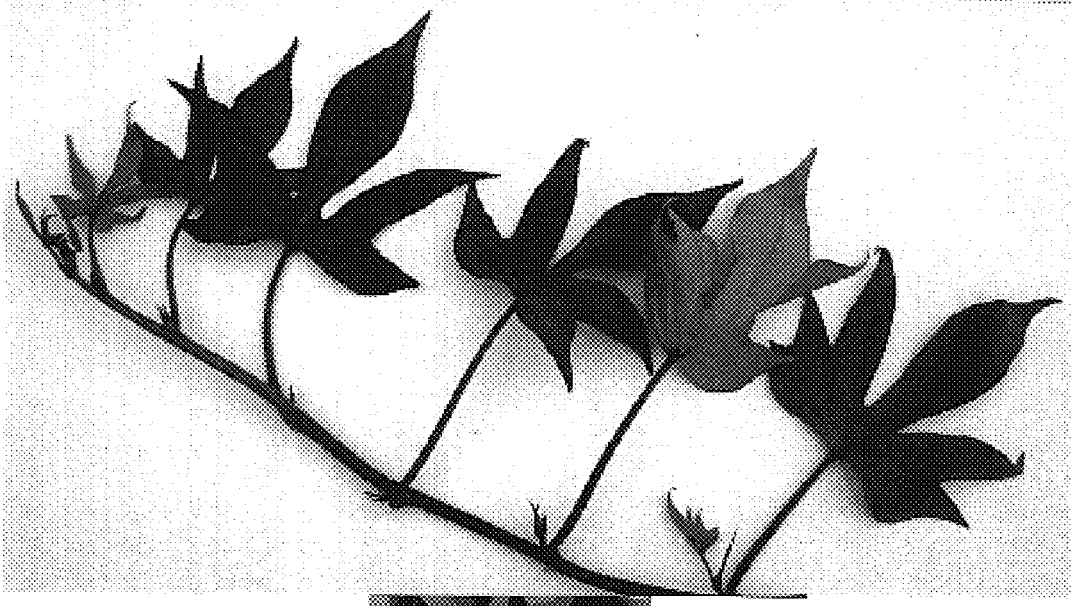
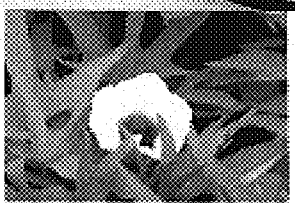

* * * * *